United States Patent
Miller et al.

(10) Patent No.: US 6,592,525 B2
(45) Date of Patent: Jul. 15, 2003

(54) MICRO-MACHINED ULTRASONIC TRANSDUCER (MUT) HAVING IMPROVED SENSITIVITY

(75) Inventors: David G. Miller, North Andover, MA (US); Bernard J. Savord, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/918,868

(22) Filed: Jul. 31, 2001

(65) Prior Publication Data

US 2003/0028103 A1 Feb. 6, 2003

(51) Int. Cl.$^7$ .................................. A61B 8/14
(52) U.S. Cl. ...................................... 600/459
(58) Field of Search ................ 600/437–472; 29/25.35; 310/363–366, 369, 311; 367/117, 105

(56) References Cited

U.S. PATENT DOCUMENTS

| | | |
|---|---|---|
| 5,146,435 A | 9/1992 | Bernstein |
| 5,569,968 A | 10/1996 | Lal et al. |
| 5,619,476 A | 4/1997 | Haller et al. ................ 367/181 |
| 5,990,677 A * | 11/1999 | Goldfine et al. ............ 324/239 |
| 6,328,696 B1 * | 12/2001 | Fraser ........................ 600/459 |
| 6,381,197 B1 * | 4/2002 | Savord et al. .............. 367/178 |
| 6,425,869 B1 * | 7/2002 | Rafter et al. ................ 600/458 |
| 6,443,901 B1 * | 9/2002 | Fraser ........................ 600/459 |

OTHER PUBLICATIONS

I. Ladabaum, X. Jin, H. Soh, A. Atalar, B. Khuri–Yakub, "Surface Micromachined Capacitive Ultrasound Transducers", IEEE Trans. Ultrason., Ferroelect., Freq. Contr., vol., pp. 678–690, May 1998.

"A Micromachined Condenser Hydrophone", J. Bernstein, Solid–State Sensor and Actuator Workshop, 1992, 5$^{th}$ Techn. Digest, IEEE Hilton Head Island SC US Jun. 22–25 1992, New York NY USA IEEE US, ISBN 0–7803–04560X.

* cited by examiner

Primary Examiner—Francis J. Jaworski
Assistant Examiner—William C Jung
(74) Attorney, Agent, or Firm—John Vodopia

(57) ABSTRACT

An AC biasing arrangement for a micro-machined ultrasonic transducer (MUT) is disclosed. The AC biasing arrangement allows the sensitivity of each MUT element in an array to be adjusted without collapsing the MUT membrane. The sensitivity of the MUT element can be adjusted by varying the frequency of the AC bias signal supplied to the MUT element. An alternative embodiment of the invention adds a second AC bias signal having a phase opposite the phase of the first AC bias signal. This arrangement provides a neutral bias signal, thereby removing the large amplitude bias signal from the MUT element.

27 Claims, 3 Drawing Sheets

MICRO-MACHINED ULTRASONIC TRANSDUCER (MUT) HAVING IMPROVED SENSITIVITY

TECHNICAL FIELD

The present invention relates generally to ultrasonic transducers, and, more particularly, to an AC biased micro-machined ultrasonic transducer (MUT) having improved sensitivity.

BACKGROUND OF THE INVENTION

Ultrasonic transducers have been available for quite some time and are particularly useful for non-invasive medical diagnostic imaging. Ultrasonic transducers are typically formed of either piezoelectric elements or of micro-machined ultrasonic transducer (MUT) elements. The piezoelectric elements typically are made of a piezoelectric ceramic such as lead-zirconate-titanate (PZT), with a plurality of elements being arranged to form a transducer. A MUT is formed using known semiconductor manufacturing techniques resulting in a capacitive ultrasonic transducer cell that comprises, in essence, a flexible membrane supported around its edges over a silicon substrate by an insulating material. By applying contact material, in the form of electrodes, to the membrane, or a portion of the membrane, and to the base of the cavity in the silicon substrate, and then applying appropriate voltage signals to the electrodes, the MUT may be energized such that an appropriate ultrasonic wave is produced. Similarly, when electrically biased, the membrane of the MUT may be used to receive ultrasonic signals by capturing reflected ultrasonic energy and transforming that energy into movement of the electrically biased membrane, which then generates a receive signal.

The ultrasonic transducer elements may be combined with control circuitry forming a transducer assembly, which is then further assembled into a housing possibly including additional control electronics, in the form of electronic circuit boards, the combination of which forms an ultrasonic probe. This ultrasonic probe, which may include various acoustic matching layers, backing layers, and de-matching layers may then be used to send and receive ultrasonic signals through body tissue.

MUT arrays are typically designed where each MUT element is a transceiver. In such an arrangement, each MUT element both produces a transmit pulse and receives acoustic energy. Unfortunately, the characteristics of a MUT element that make it a good transmitter of acoustic energy are not the same characteristics that make it a good receiver of acoustic energy. For example, during a transmit pulse, it is desirable for the MUT to provide a large power output. To accomplish this, a large membrane deflection, a large gap, high membrane stiffness, and high bias voltage are used to produce the high pressure wave desired on transmit. In such a MUT, the cavity depth should be at least three times deeper than the static deflection of the membrane. Membrane deflection larger than approximately ⅓ of the cavity depth results in the collapse of the membrane against the cavity floor. The gap is defined as the distance between the membrane and the bottom of the cavity. A large gap results in a small capacitance and large imaginary impedance.

Conversely, for a MUT to be a sensitive acoustic receiver, a small membrane deflection, a small gap, low membrane stiffness, and high bias voltage are used to produce a sensitive acoustic receiver element. In the past, a DC bias voltage has typically been applied to deflect the membrane and reduce the gap to the minimum uncollapsed size. The small gap reduces the imaginary impedance and the soft membrane deflects easily when exposed to acoustic energy reflected from a target resulting in a high signal-to-noise ratio (SNR). During receive operation the DC bias voltage functions as a "sense" voltage and the current (I) through the MUT is monitored so that the capacitance (C) of the MUT can be measured. The charge (Q) on the MUT is defined as $Q=C*V$, where C is the capacitance of the MUT and V is the DC bias voltage applied to the MUT. The current (I) is defined as $I=dQ/dt,=d[C \times V]/dt$.

Unfortunately, the application of a DC bias voltage to the MUT during receive operation has drawbacks. For example, in order to increase the receive sensitivity of the MUT, the DC bias voltage should be increased. Unfortunately, once the DC bias voltage reaches a certain point, commonly referred to as the collapse voltage, $V_{collapse}$, the MUT membrane collapses against the floor of the cavity and becomes inoperable as a receiver. Therefore, when using a DC bias voltage, the sensitivity of the MUT is limited by $I=dC/dt*V_{collapse}$.

Therefore, it would be desirable to have the ability to adjust the sensitivity of a MUT without this limitation on bias voltage.

SUMMARY

An AC biasing arrangement for a micro-machined ultrasonic transducer (MUT) is disclosed. The AC biasing arrangement allows the sensitivity of each MUT element in an array to be adjusted without collapsing the MUT membrane. The sensitivity of the MUT element can be adjusted by varying the frequency of the AC bias signal supplied to the MUT element. An alternative embodiment of the invention adds a second AC bias signal having a phase opposite the phase of the first AC bias signal. This arrangement provides a neutral bias signal, thereby removing the large amplitude bias signal from the MUT element.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE INVENTION

The invention described hereafter is applicable to many different configurations of micro-machined ultrasonic transducer (MUT) elements connected to biasing circuitry. The configuration shown below is merely one possible example of using an AC signal to bias a MUT element.

Figure 1:
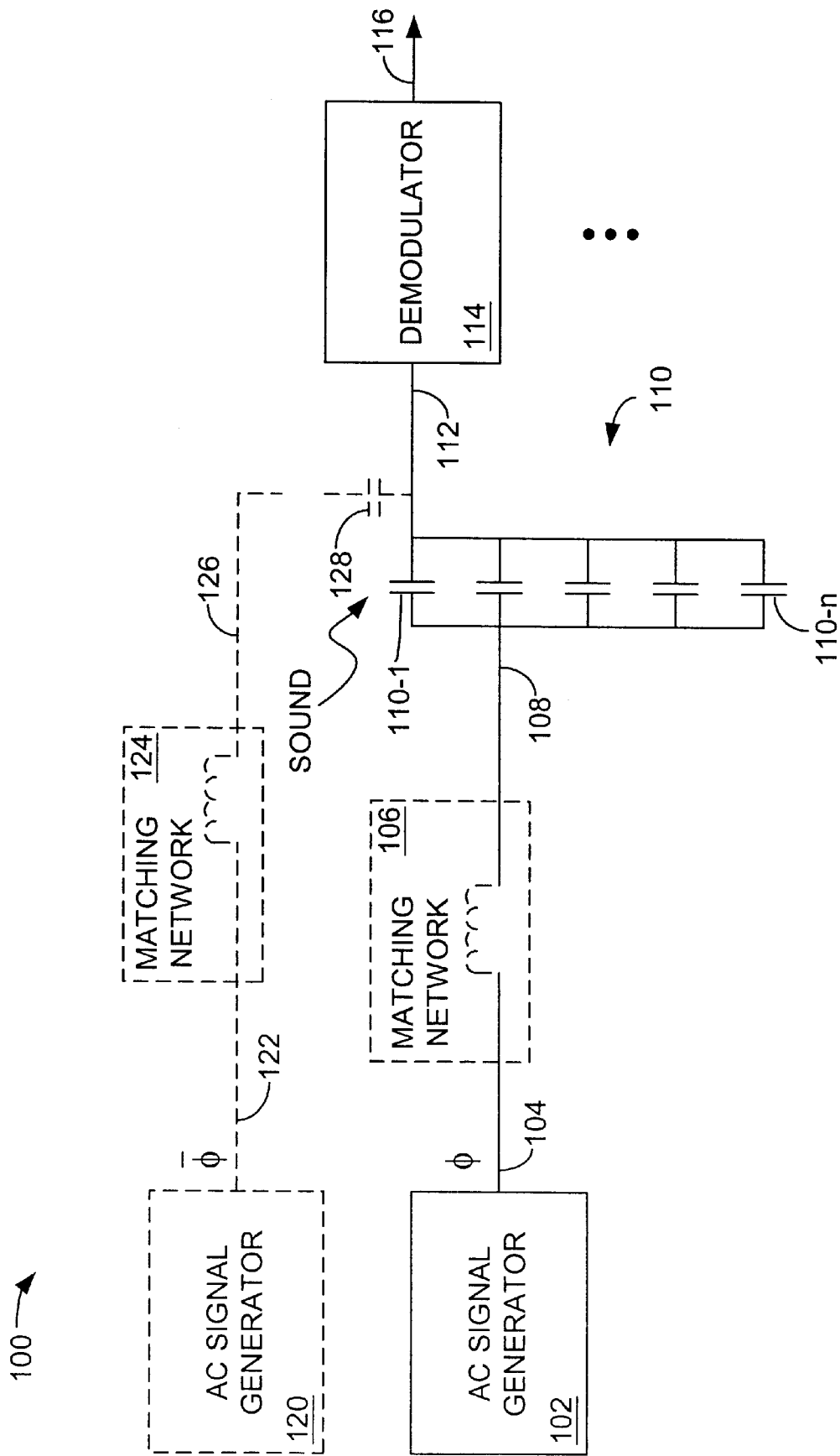
FIG. 1 is a block diagram illustrating a portion of a micro-machined ultrasonic transducer (MUT) receiver.

FIG. 1 is a block diagram illustrating a portion of a micro-machined ultrasonic transducer (MUT) acoustic receiver 100. The MUT acoustic receiver 100 includes an AC signal generator 102 coupled via connection 104 to an optional matching network 106. The AC signal generator 102 provides an AC sense signal on connection 104. The AC sense signal, referred to as an AC bias signal, is used to electrically bias the MUT elements in a MUT array 110. The AC sense signal, referred to as $\phi$, is typically generated at a frequency that is generally higher than twice the acoustic sensor frequency of the MUT receive signal.

If the optional matching network 106 is omitted, then the AC sense signal is communicated via connection 108 to MUT array 110. MUT array 110 typically includes a plurality of individual MUT elements 110-$l$ through 110-$n$. Because the MUT elements are characterized by their capacitance, the MUT elements 110-$l$ through 110-$n$ are schematically illustrated as capacitors. Typically, a MUT array 110 can include many hundreds or thousands of MUT elements, but for ease of connectivity, typically includes arrays of 128 elements. Further, although the detail of which is omitted for simplicity, each MUT element 110-$l$ through 110-$n$ typically includes a plurality of MUT cells. The MUT cells in each MUT element 110-$l$ through 110-$n$ can be connected either in series or parallel depending upon the desired performance.

Further, although shown as using a single AC signal generator 102 coupled to the MUT array 110, it is possible that individual AC signal generators may be coupled to each MUT element 110-$l$ through 110-$n$. However, for simplicity, a single AC generator 102 is shown as coupled to the MUT array 110 in FIG. 1. In accordance with an aspect of the invention, each MUT element 110-$l$ through 110-$n$ is electrically biased using the AC sense signal $\phi$ on connection 108. The output of the AC signal generator 102 on connection 104 can be any appropriate waveform as known to those having ordinary skill in the art, and can be, for example but not limited to, a square wave or a sine wave.

During receive operation, sound impinges on each MUT element 110-$l$ through 110-$n$. Because each MUT element is biased with an AC signal, there is no collapse voltage, and therefore, the set point of the membrane of the MUT remains relatively stable. In this manner, the sensitivity of the MUT can be adjusted as a function of the frequency of the signal $\phi$ on connection 108.

When an AC sense signal is used to bias the MUT elements 110-$l$ through 110-$n$, the current is defined by the equation I=C*dV/dt. Therefore, the sensitivity of each MUT element 110-$l$ through 110-$n$ increases as dt decreases and as the frequency of the AC sense signal $\phi$ increases. Preferably, the frequency of the AC sense signal on connection 108 is at a sufficiently high frequency so that the membrane of each MUT cell within each MUT element 110-$l$ through 110-$n$ is either static, or moving very slowly. Therefore, the current through the MUT element depends on the slew rate of the voltage of the AC sense signal. In this manner, the desired sensitivity of each MUT element 110-$l$ through 110-$n$ can be adjusted by increasing or decreasing the frequency of the AC sense signal on connection 108.

The optional matching network 106 provides a controlled impedance that can match the impedance of the output of the AC signal generator 102 to the impedance of the MUT array 110. Furthermore, the optional matching network 106 can be used to raise the voltage level of the signal on connection 104 to increase the sensitivity of the MUT array 110. The optional matching network may be a simple series inductor or a parallel inductor, a complex inductive-capacitive (LC) network, a pi ($\pi$) network, a tee network, or, if active control of the voltage on connection 104 is desired, a transformer. If the matching network 106 includes a transformer, then the voltage level of the signal on connection 104 can be increased so that the sensitivity of the MUT array 110 is also increased.

During operation, sound impinges on each MUT element 110-$l$ through 110-$n$. The sound causes the membrane of the MUT to vibrate, thereby providing an electrical signal output of the MUT on connection 112. This electrical signal is a result of and proportional to the sound impinging on the MUT element 110-$l$. The variation of the electrical signal on connection 112 due to the sound impinging on the MUT element 110-$l$ is then supplied to a demodulator 114. The demodulator 114 demodulates the signal on connection 112 and provides an output on connection 116 to additional receive and processing circuitry (not shown), and eventually to the display (not shown) of the ultrasound unit in which the MUT acoustic receiver 100 is located. Three exemplar embodiments of the demodulator 114 will be described with respect to FIGS. 2A, 2B and 2C.

Due to the relatively large AC sense signal on connection 108, the level of the voltage signal on connection 112 is large and will vary with the capacitance variation of each MUT element 110-$l$ through 110-$n$. This capacitance variation is a result of the sound impinging on the MUT element 110-$l$ and is the signal of interest because it represents the sound impinging on each MUT element 110-$l$ through 110-$n$. In order to reduce or eliminate the large AC sense signal present at connection 112, a second AC signal generator 120 can be used. The AC signal generator 120 provides an AC signal having substantially the same amplitude as the output of AC signal generator 102, but having an opposite phase. This opposite phase AC signal, denoted as the inverse of $\phi$, is supplied via connection 122 to optional matching network 124. The optional matching network 124 is shown as a single inductor for simplicity. Typically, the configuration of the optional matching network 124 will be similar to the configuration of the optional matching network 106.

The output of the optional matching network 124 is supplied via connection 126 to an optional fixed capacitor 128. If the amplitude of the inverse $\phi$ signal output from the AC signal generator 120 is substantially equal to the amplitude of the $\phi$ signal output from the AC signal generator 102, then the capacitance value of the optional fixed capacitor 128 should be substantially equal to the capacitance of the AC biased MUT element 110-$l$. Alternatively, depending on the amplitude of the inverse $\phi$ signal, the capacitance value of the optional capacitor 128 may vary from the capacitance value of the MUT element 110-$l$. Further, although only a single fixed capacitor is illustrated in FIG. 1, there will typically be a fixed capacitor 128 for each MUT element 110-$l$ through 110-$n$.

By adding the inverse $\phi$ signal from the optional AC signal generator 120, the large $\phi$ signal (the AC sense signal) present on connection 112 is cancelled, leaving only the capacitance variation signal of the MUT element 110-$l$ on connection 112. This variation signal is the result of the sound impinging on the MUT element 110-$l$. Therefore, ideally, there is substantially no signal present on connection 112 when the MUT element 110-$l$ is in its biased reference position. When the membrane of the MUT element 110-$l$ moves due to sound impinging on it, the variation signal that is generated by the sound is the only signal present on connection 112. This variation signal (i.e., the signal of interest) is then demodulated by the demodulator 114. Essentially, there is no signal present on connection 112 until the membrane of the MUT element 110-*l* moves. This arrangement can help prevent the MUT acoustic receiver 100 from saturating.

In order to conserve resources and maximize the use of the space available on the substrate upon which the MUT array 110 is formed, the fixed capacitor 128 can be fabricated on the same substrate as each MUT element 110-*l* through 110-*n*. This arrangement will be illustrated below with respect to FIG. 3.

Figure 2A:
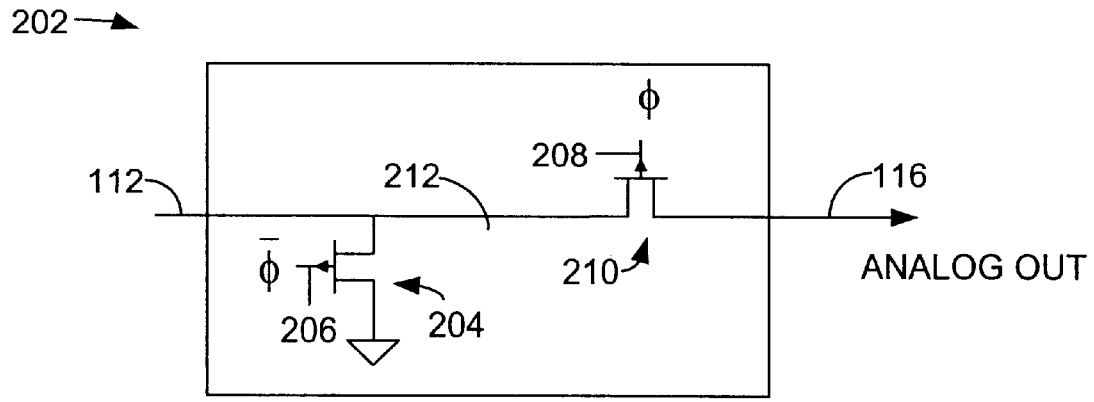
FIG. 2A is a schematic diagram illustrating a first embodiment of the demodulator of FIG. 1.

FIG. 2A is a schematic diagram illustrating a first embodiment of the demodulator 114 of FIG. 1. The demodulator 202 of FIG. 2A is an analog demodulator that includes a pair of switches 204 and 210. The switches 204 and 210 can be implemented using, for example but not limited to, field effect transistor (FET) technology. The switch 204 receives a clock signal at the gate terminal 206. The clock signal has a frequency that is the same as the frequency of the inverse φ signal from the AC signal generator 120, and can indeed be the inverse φ signal from the AC signal generator 120. The clock signal on gate terminal 206 causes the switch 204 to close and the current on connection 112 is shorted to ground.

The switch 210 receives a clock signal that has a frequency that is the same as the frequency of the φ signal from the AC signal generator 102, and can indeed be the φ signal from the AC signal generator 102. When the φ signal is applied to the gate terminal 208 of the switch 210, the signal input on connection 112 is sampled at its peak and routed via connection 212 to connection 116, becoming the analog output of the demodulator.

Figure 2B:
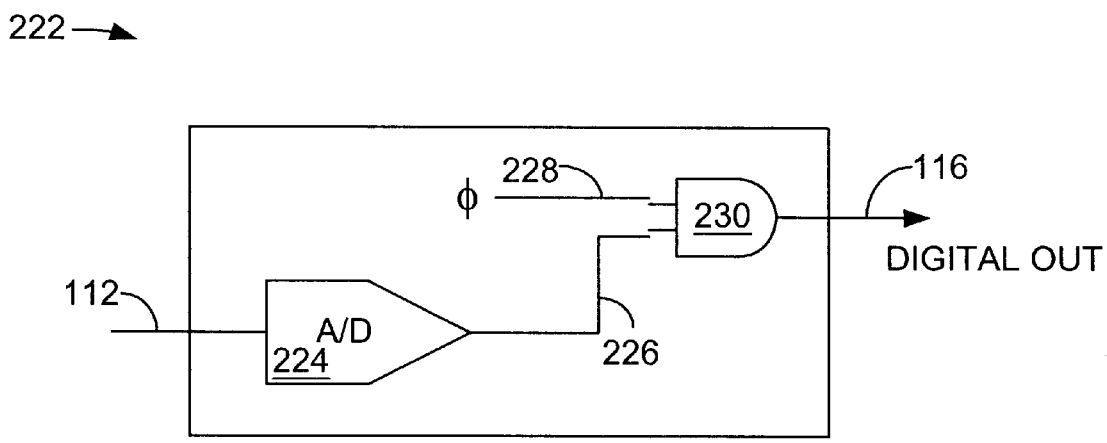
FIG. 2B is a schematic view illustrating an alternative embodiment of the demodulator of FIG. 1.

FIG. 2B is a schematic view illustrating an alternative embodiment of the demodulator 114 of FIG. 1. The demodulator 222 of FIG. 2B includes an analog-to-digital (A/D) converter 224 and an AND gate 230. The A/D converter 224 has a sample rate and if there is an AC signal present on connection 112 and the A/D converter is synchronous with that AC signal, then by sampling the AC signal at its peak, the AC signal is demodulated. In this manner, the output of the MUT element 110-*l* (FIG. 1A) on connection 112 is demodulated. This demodulated signal is then forwarded via connection 226 to one of the inputs of the AND gate 230. The other input to the AND gate 230 is the φ signal on connection 228. In this manner, a digital output is provided on connection 116.

Figure 2C:
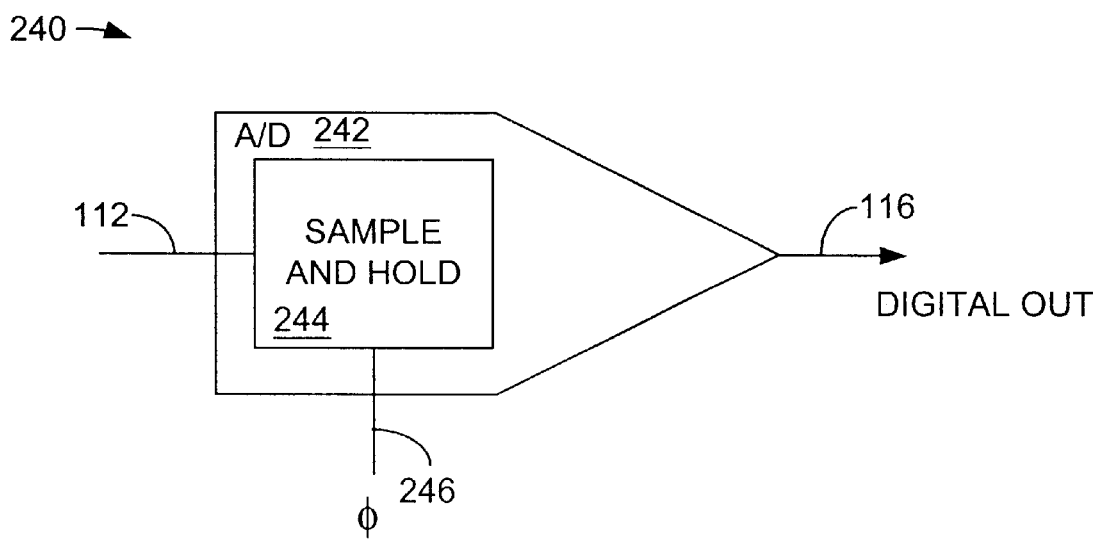
FIG. 2C is another alternative embodiment of the demodulator of FIG. 1.

FIG. 2C is another alternative embodiment of the demodulator 114 of FIG. 1. The demodulator 240 includes an A/D converter 242, which includes a sample and hold circuit 244. The sample and hold circuit 244 is essentially the demodulator, whereby the AC signal present on connection 112 is sampled in accordance with the assertion of the φ signal on connection 246. The output of the A/D converter 242 on connection 116 is the demodulated digital output, which is then forwarded to the other elements of the MUT acoustic receiver.

Figure 3:
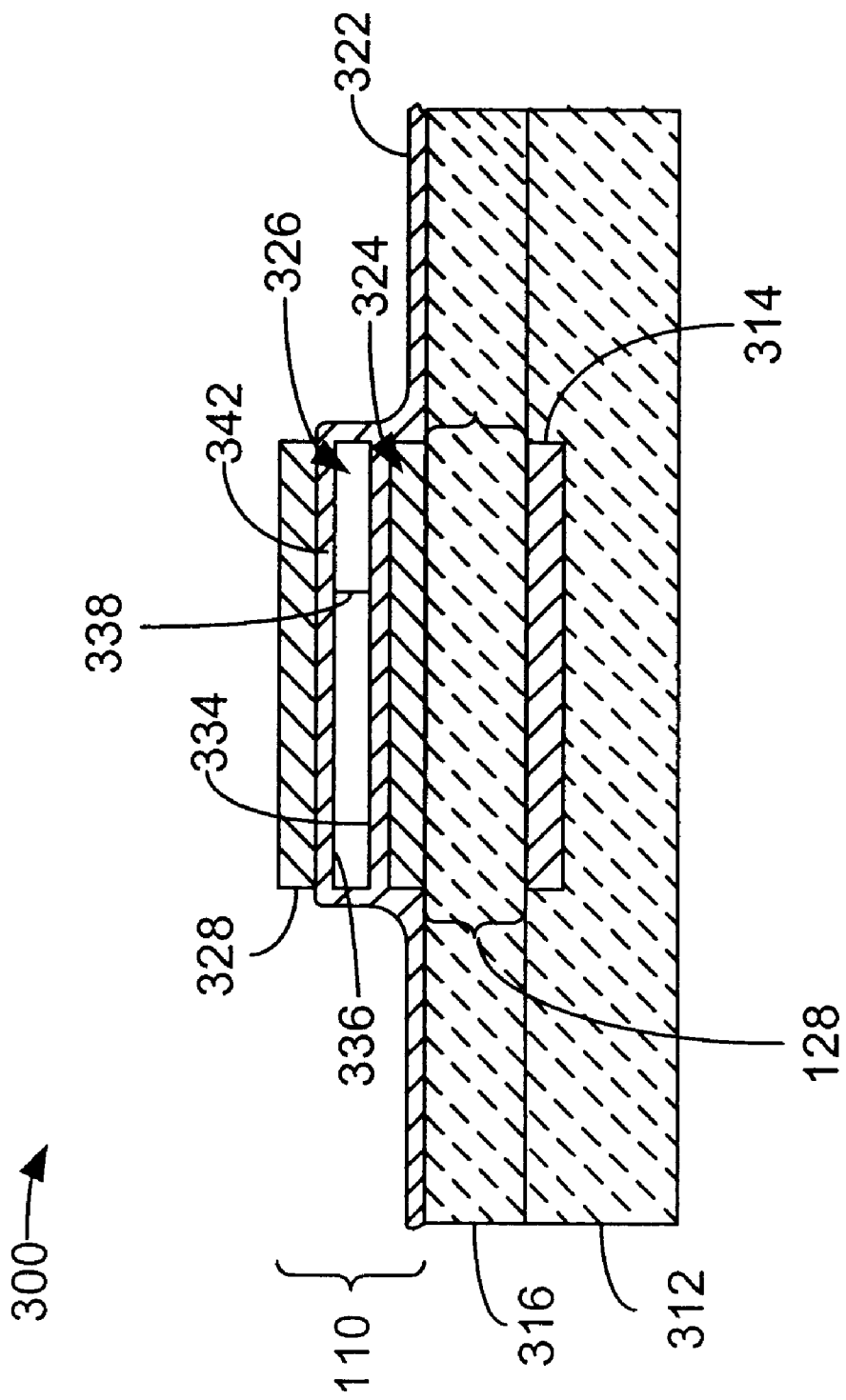
FIG. 3 is a cross-sectional schematic view of a micro-machined ultrasonic transducer (MUT) cell assembly including a fixed capacitor in accordance with an aspect of the invention.

FIG. 3 is a cross-sectional schematic view of a micromachined ultrasonic transducer (MUT) cell assembly including a fixed capacitor in accordance with an aspect of the invention. Many techniques can be used to build MUT cells in many configurations, and the configuration shown in FIG. 3 is merely illustrative. The MUT cell assembly 300 generally includes a substrate material 312 of silicon (Si) that includes, for this example, an N+ doped conductor 314.

A dielectric layer 316 of, for example, silicon nitride (SiN) is deposited over the substrate layer 312. A metal conductor 324 is deposited over the dielectric 316 as shown. The MUT cell 110 is formed over the dielectric layer 316 and the metal conductor 324.

The MUT cell 110 includes a membrane 322, preferably constructed using silicon nitride, that is applied over the dielectric layer 316 and the metal conductor 324 forming a cavity 326, sometimes referred to as a vacuum gap. The portion 342 of the membrane 322 that forms the cavity 326 is flexible. The cavity 326 defines a gap 338, which is the distance between the base of the cavity, referred to as the cavity floor 334 and the lower surface 336 of the flexible membrane portion 342.

An electrical contact 328 is applied over the flexible membrane portion 342 as shown in order to provide electrical connectivity to the cavity 326, which acts as a variable capacitor. The flexible membrane portion 342 is sufficiently flexible so that it can deflect in response to electrical signals applied through the electrical contacts 324 and 328, and in response to acoustic energy impinging on the flexible membrane portion 342.

In accordance with an aspect of the invention, the fixed capacitor 128 of FIG. 1 is formed by the dielectric layer 316 that exists between the N+ doped conductor 314 and the metal conductor 324. In this manner, the fixed capacitor 128 can be vertically integrated with the MUT cell 110 and the fixed capacitor 128 and the MUT cell 110 can share the metal conductor 324. The circuitry that supplies electrical signals to the electrical contacts 314, 324 and 328 to bias the MUT cell assembly 300 is omitted from the drawings for simplicity.

It will be apparent to those skilled in the art that many modifications and variations may be made to the present invention, as set forth above, without departing substantially from the principles of the present invention. For example, the present invention can be used with many different configurations of MUT transducer elements. Furthermore, the invention is applicable to different substrate materials including, for example, silicon and germanium. All such modifications and variations are intended to be included herein.

What is claimed is:

1. A micro-machined ultrasonic transducer (MUT) acoustic receiver, comprising:
   a MUT having a capacitance and configured to receive sonic energy and to convert the sonic energy into an electrical signal;
   a first AC signal generator configured to supply an AC bias signal to the MUT, the AC bias signal having a phase; and
   a demodulator configured to receive a combined signal including the electrical signal and AC bias signal output of the MUT, the demodulator configured to receive the AC bias signal or a signal having the same frequency as the AC bias signal, the demodulator further configured to demodulate the combined signal.

2. The MUT acoustic receiver of claim 1, wherein the demodulator provides an analog output.

3. The MUT acoustic receiver of claim 1, wherein the demodulator provides a digital output.

4. The MUT acoustic receiver of claim 3, wherein the demodulator includes an analog-to-digital (A/D) converter.

5. The MUT acoustic receiver of claim 1, further comprising:
   a second AC signal generator configured to supply an AC bias signal having a phase opposite the phase of the AC bias signal provided by the first AC signal generator; and a capacitive element coupled to the output of the second AC signal generator, where the output of the capacitive element is supplied to the demodulator.

6. The MUT acoustic receiver of claim 5, wherein the capacitive element is arranged in parallel with the MUT.

7. The MUT acoustic receiver of claim 6, wherein the capacitive element is a fixed capacitor.

8. The MUT acoustic receiver of claim 6, wherein the capacitive element is fabricated on the same substrate as the MUT.

9. The MUT acoustic receiver of claim 8, wherein the capacitive element and the MUT are vertically oriented and share a common electrode.

10. The MUT acoustic receiver of claim 1, further comprising an impedance matching network coupled between the first AC signal generator and the MUT.

11. The MUT acoustic receiver of claim 10, wherein the impedance matching network includes at least one inductive element.

12. The MUT acoustic receiver of claim 11, wherein the impedance matching network is a transformer.

13. The MUT acoustic receiver of claim 11, wherein the impedance matching network is adjustable.

14. A method for biasing a micro-machined ultrasonic transducer (MUT) acoustic receiver, comprising:
   providing a MUT having a capacitance, the MUT configured to receive sonic energy and to convert the sonic energy into an electrical signal;
   supplying a first AC bias signal to the MUT, the AC bias signal having a phase; and
   demodulating a combined signal including the electrical signal and AC bias signal that is output of the MUT by a demodulator configured to receive the first AC bias signal or a signal having the same frequency as the first AC bias signal.

15. The method of claim 14, wherein said demodulating step comprises providing the demodulated combined electrical and AC bias signal as an analog output.

16. The method of claim 14, wherein said demodulating step comprises providing the demodulated combined electrical and AC bias signal as a digital output.

17. The method of claim 14, further comprising:
   supplying a second AC bias signal having a phase opposite the phase of the first AC bias signal to a capacitive element; and
   coupling the capacitive element to the demodulator, where the second AC bias signal and the capacitive element substantially eliminate the first AC bias signal.

18. The method of claim 17, further comprising arranging the capacitive element in parallel with the MUT.

19. The method of claim 18, wherein said arranging step comprises arranging said the capacitive element as a fixed capacitor.

20. The method of claim 18, further comprising fabricating the capacitive element on the same substrate as the MUT.

21. The method of claim 20, further comprising vertically orienting the capacitive element and the MUT so that the capacitive element and the MUT share a common electrode.

22. The method of claim 14, further comprising coupling an impedance matching network between the first AC signal generator and the MUT.

23. The method of claim 22, wherein said coupling step comprises the coupling impedance matching network to include at least one inductive element.

24. The method of claim 23, wherein the coupling step comprises coupling the impedance matching network as a transformer.

25. The method of claim 23, wherein the coupling step comprises coupling the impedance matching network so as to be adjustable.

26. A micro-machined ultrasonic transducer (MUT) acoustic receiver, comprising:
   a MUT having a capacitance and configured to receive sonic energy and to convert the sonic energy into an electrical signal;
   a first AC signal generator configured to supply a first AC bias signal to the MUT, the first AC bias signal having a phase;
   a second AC signal generator configured to supply a second AC bias signal to the MUT, the second AC bias signal having a phase that is opposite the phase of the first AC bias signal;
   a capacitor coupled between the second AC signal generator and the MUT; and
   a demodulator configured to receive and demodulate the electrical signal, the demodulator further configured to receive the first AC bias signal or a signal having the same frequency as the first AC bias signal.

27. The MUT acoustic receiver of claim 26, further comprising:
   a first impedance matching network coupled between the first AC signal generator and the MUT; and
   a second impedance matching network coupled between the second AC signal generator and the capacitor.

* * * * *